US008583260B2

(12) United States Patent
Knudson

(10) Patent No.: US 8,583,260 B2
(45) Date of Patent: Nov. 12, 2013

(54) LONG TRAVEL STEERABLE CATHETER ACTUATOR

(75) Inventor: John C. Knudson, Chanhassen, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 2861 days.

(21) Appl. No.: 11/024,181

(22) Filed: Dec. 28, 2004

(65) Prior Publication Data

US 2006/0142695 A1 Jun. 29, 2006

(51) Int. Cl.
*A61N 1/00* (2006.01)
(52) U.S. Cl.
USPC ........ 607/122; 604/95.04; 604/264; 604/523; 604/528; 604/41; 604/47; 604/48; 600/585; 600/374
(58) Field of Classification Search
USPC ............ 604/95.04, 264, 523, 528, 41, 47–50; 600/585, 374
See application file for complete search history.

(56) References Cited

U.S. PATENT DOCUMENTS

| 4,941,455 | A | * | 7/1990 | Watanabe et al. | 600/146 |
|---|---|---|---|---|---|
| 4,947,827 | A | * | 8/1990 | Opie et al. | 600/108 |
| 4,960,134 | A | | 10/1990 | Webster, Jr. | 128/786 |
| 5,125,895 | A | | 6/1992 | Buchbinder et al. | 604/95 |
| 5,125,896 | A | | 6/1992 | Hojeibane | 604/95 |
| 5,163,942 | A | * | 11/1992 | Rydell | 606/113 |
| 5,195,968 | A | * | 3/1993 | Lundquist et al. | 604/95.04 |
| 5,269,757 | A | | 12/1993 | Fagan et al. | 604/95 |
| RE34,502 | E | | 1/1994 | Webster, Jr. | 607/125 |
| 5,277,199 | A | | 1/1994 | DuBois et al. | 128/772 |
| 5,281,217 | A | | 1/1994 | Edwards et al. | 606/41 |
| 5,318,525 | A | | 6/1994 | West et al. | 604/95 |
| 5,327,889 | A | | 7/1994 | Imran | 128/642 |
| 5,327,905 | A | | 7/1994 | Avitall | 128/772 |

(Continued)

FOREIGN PATENT DOCUMENTS

| EP | 1 205 208 | 5/2002 |
|---|---|---|
| GB | 1 170 018 | 11/1969 |

*Primary Examiner* — Nicholas Lucchesi
*Assistant Examiner* — Scott Medway
(74) *Attorney, Agent, or Firm* — Wiley Rein LLP

(57) ABSTRACT

The present invention is an electrophysiology, RF ablation, or similar catheter (i.e., catheter or sheath) that includes an actuator that significantly increases the length of travel (i.e., steering travel) of the actuation wires, as compared to the length of travel provided by prior art actuators. The catheter includes a hollow flexible tubular body, a pair of actuation wires disposed in a side-by-side relationship in the body, a handle attached to a proximal end of the body, an actuator pivotally mounted to the handle, an arcuate internal gear rack disposed on the actuator, one or more pulleys pivotally mounted on the handle and coaxially coupled to a pinion gear engaged with the gear rack, and a guide block mounted within the handle. The one or more pulleys include a first channel in which the first actuation wire resides and a second channel in which the second actuation wire resides. The actuation wires pass through holes in the guide block, which aligns the wires into their respective channels. The actuation wires enter into their respective channels on opposite sides of the axis of the one or more pulleys. As the actuator is pivoted relative to the handle, the gear rack rotates the pinion gear and the one or more pulleys. This causes one of the actuation wires to be in-hauled (i.e., wound about the one or more pulleys) and the other actuation wire to be paid-out (i.e., unwound from the one or more pulleys).

10 Claims, 9 Drawing Sheets

(56) References Cited

U.S. PATENT DOCUMENTS

| | | |
|---|---|---|
| 5,327,906 A | 7/1994 | Fideler et al. |
| 5,330,466 A | 7/1994 | Imran ............................. 606/13 |
| 5,342,295 A | 8/1994 | Imran ............................. 604/43 |
| 5,354,297 A | 10/1994 | Avitall .......................... 606/45 |
| 5,364,351 A | 11/1994 | Heinzelman et al. |
| 5,383,923 A | 1/1995 | Webster, Jr. .................. 607/125 |
| 5,389,073 A | 2/1995 | Imran ............................. 604/95 |
| 5,391,147 A | 2/1995 | Imran et al. .................... 604/95 |
| 5,395,328 A | 3/1995 | Ockuly et al. .................. 604/95 |
| 5,395,329 A | 3/1995 | Fleischhacker et al. ........ 604/95 |
| 5,397,304 A | 3/1995 | Truckai ............................ 604/95 |
| 5,409,453 A * | 4/1995 | Lundquist et al. ............... 604/22 |
| 5,431,168 A | 7/1995 | Webster, Jr. .................. 128/658 |
| 5,445,148 A | 8/1995 | Jaraczewski et al. ........ 128/642 |
| 5,478,330 A | 12/1995 | Imran et al. .................... 604/282 |
| 5,479,930 A * | 1/1996 | Gruner et al. ................. 600/459 |
| 5,487,385 A | 1/1996 | Avitall .......................... 128/642 |
| 5,487,757 A | 1/1996 | Truckai et al. ................ 607/122 |
| 5,527,279 A | 6/1996 | Imran ............................. 604/95 |
| 5,533,967 A | 7/1996 | Imran ............................. 604/95 |
| 5,545,200 A | 8/1996 | West et al. .................... 607/122 |
| 5,562,619 A | 10/1996 | Mirarchi et al. ................ 604/95 |
| 5,582,609 A | 12/1996 | Swanson et al. ................ 606/39 |
| 5,588,964 A | 12/1996 | Imran et al. .................... 604/95 |
| 5,611,777 A | 3/1997 | Bowden et al. ................. 604/95 |
| 5,626,136 A | 5/1997 | Webster, Jr. .................. 128/642 |
| 5,656,029 A | 8/1997 | Imran et al. .................... 604/95 |
| 5,656,030 A | 8/1997 | Hunjan et al. ................. 604/95 |
| 5,667,488 A * | 9/1997 | Lundquist et al. ............... 604/22 |
| 5,755,760 A | 5/1998 | Maguire et al. ............... 607/122 |
| 5,779,669 A | 7/1998 | Haissaguerre et al. ........ 604/95 |
| 5,807,249 A | 9/1998 | Qin et al. ....................... 600/374 |
| 5,826,576 A | 10/1998 | West ............................. 128/642 |
| 5,827,272 A | 10/1998 | Breining et al. ................ 606/41 |
| 5,827,278 A | 10/1998 | Webster .......................... 606/41 |
| 5,836,947 A | 11/1998 | Fleischman et al. ........... 606/47 |
| 5,842,984 A | 12/1998 | Avitall .......................... 600/374 |
| 5,843,031 A | 12/1998 | Hermann et al. ............... 604/95 |
| 5,843,076 A | 12/1998 | Webster, Jr. et al. ........... 606/41 |
| 5,861,024 A | 1/1999 | Rashidi et al. |
| 5,865,800 A | 2/1999 | Mirarchi et al. ................ 604/95 |
| 5,885,278 A | 3/1999 | Fleischman et al. ........... 606/41 |
| 5,897,529 A | 4/1999 | Ponzi ............................. 604/95 |
| 5,910,129 A | 6/1999 | Koblish et al. ................. 604/95 |
| 5,916,213 A | 6/1999 | Haissaguerre et al. ........ 606/41 |
| 5,916,214 A | 6/1999 | Cosio et al. ..................... 606/41 |
| 5,921,924 A | 7/1999 | Avitall .......................... 600/374 |
| 5,931,811 A | 8/1999 | Haissaguerre et al. ........ 604/95 |
| 5,935,102 A | 8/1999 | Bowden et al. ................. 604/95 |
| 5,944,690 A | 8/1999 | Falwell et al. .................. 604/95 |
| 5,987,344 A | 11/1999 | West ............................. 600/373 |
| 5,993,462 A | 11/1999 | Pomeranz et al. ............. 606/129 |
| 6,002,955 A | 12/1999 | Willems et al. ............... 600/374 |
| 6,024,722 A | 2/2000 | Rau et al. |
| 6,027,473 A | 2/2000 | Ponzi ............................. 604/95 |
| 6,033,403 A | 3/2000 | Tu et al. .......................... 606/41 |
| 6,048,329 A | 4/2000 | Thompson et al. ............. 604/95 |
| 6,059,739 A | 5/2000 | Baumann ...................... 600/585 |
| 6,064,902 A | 5/2000 | Haissaguerre et al. ........ 600/381 |
| 6,066,125 A | 5/2000 | Webster, Jr. .................. 604/528 |
| 6,068,629 A | 5/2000 | Haissaguerre et al. ........ 606/41 |
| 6,071,274 A | 6/2000 | Thompson et al. ............. 604/528 |
| 6,071,279 A | 6/2000 | Whayne et al. ................ 606/41 |
| 6,071,282 A | 6/2000 | Fleischman ..................... 606/41 |
| 6,083,222 A | 7/2000 | Klein et al. ..................... 606/41 |
| 6,090,104 A | 7/2000 | Webster, Jr. .................. 606/41 |
| 6,123,699 A | 9/2000 | Webster, Jr. .................. 604/528 |
| 6,138,043 A | 10/2000 | Avitall .......................... 600/377 |
| 6,146,355 A * | 11/2000 | Biggs .......................... 604/95.01 |
| 6,149,663 A | 11/2000 | Strandberg et al. ........... 600/180 |
| 6,156,034 A | 12/2000 | Cosio et al. ..................... 606/41 |
| 6,169,916 B1 | 1/2001 | West ............................. 600/373 |
| 6,171,277 B1 * | 1/2001 | Ponzi .......................... 604/95.04 |
| 6,178,354 B1 | 1/2001 | Gibson ........................ 607/116 |
| 6,183,435 B1 | 2/2001 | Bumbalough et al. .......... 604/95 |
| 6,183,463 B1 | 2/2001 | Webster, Jr. .................. 604/528 |
| 6,198,974 B1 | 3/2001 | Webster, Jr. .................. 607/122 |
| 6,200,315 B1 | 3/2001 | Gaiser et al. .................... 606/41 |
| 6,203,507 B1 | 3/2001 | Wadsworth et al. .......... 600/585 |
| 6,203,525 B1 | 3/2001 | Whayne et al. ................ 606/41 |
| 6,210,362 B1 | 4/2001 | Ponzi .......................... 604/95.01 |
| 6,210,407 B1 | 4/2001 | Webster .......................... 606/41 |
| 6,214,002 B1 | 4/2001 | Fleischman et al. ........... 606/41 |
| 6,221,087 B1 | 4/2001 | Anderson et al. ............. 606/159 |
| 6,224,587 B1 | 5/2001 | Gibson ........................ 604/528 |
| 6,241,754 B1 | 6/2001 | Swanson et al. ............... 607/99 |
| 6,308,091 B1 | 10/2001 | Avitall .......................... 600/374 |
| 6,375,654 B1 | 4/2002 | McIntyre ....................... 606/41 |
| 6,430,426 B2 | 8/2002 | Avitall .......................... 600/374 |
| 6,440,062 B1 * | 8/2002 | Ouchi ............................ 600/146 |
| 6,454,758 B1 | 9/2002 | Thompson et al. ............. 604/528 |
| 6,485,455 B1 * | 11/2002 | Thompson et al. ........ 604/95.04 |
| 6,533,783 B1 * | 3/2003 | Tollner ............................ 606/49 |
| 6,582,536 B2 | 6/2003 | Shimada |
| 6,652,506 B2 * | 11/2003 | Bowe et al. .................... 604/523 |
| 6,695,771 B2 * | 2/2004 | Takada .......................... 600/114 |
| 7,025,759 B2 * | 4/2006 | Muller .......................... 604/528 |
| 7,465,288 B2 * | 12/2008 | Dudney et al. ............. 604/95.04 |
| 8,052,636 B2 * | 11/2011 | Moll et al. ................... 604/95.04 |
| 2004/0054322 A1 * | 3/2004 | Vargas ........................ 604/95.04 |
| 2006/0084964 A1 * | 4/2006 | Knudson et al. ................ 606/41 |
| 2008/0255540 A1 * | 10/2008 | Selkee .......................... 604/528 |

\* cited by examiner

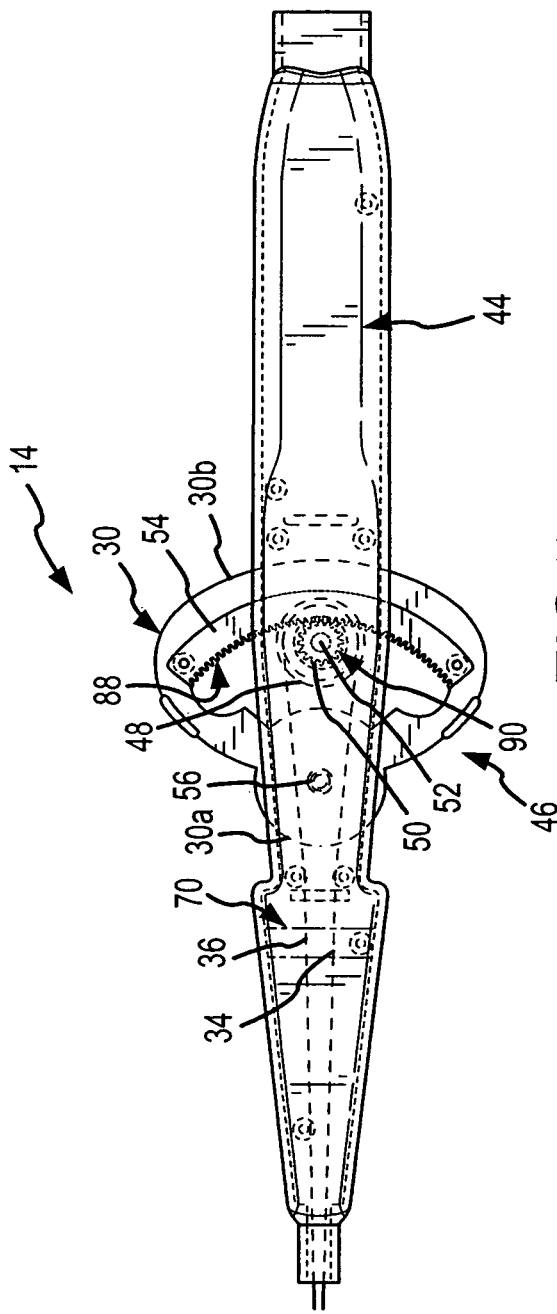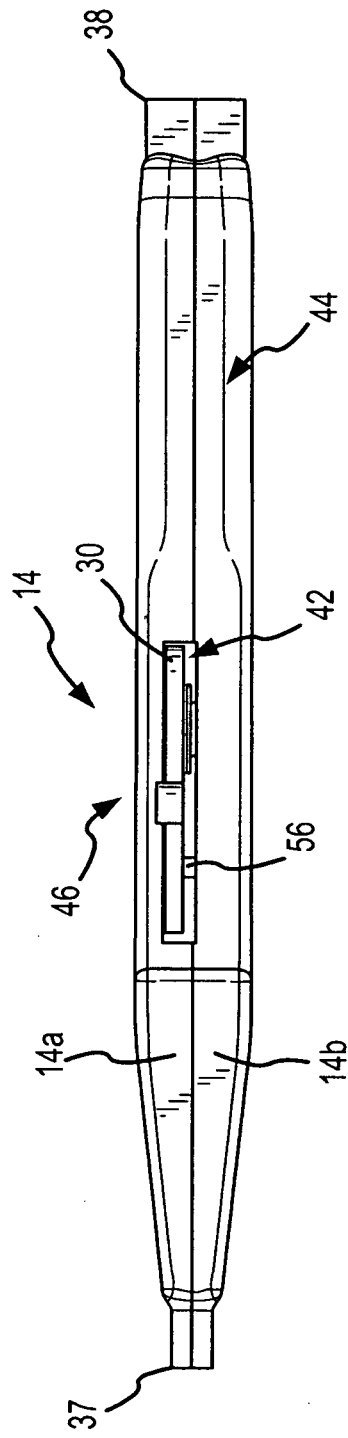

LONG TRAVEL STEERABLE CATHETER ACTUATOR

FIELD OF THE INVENTION

The present invention relates to catheters and sheaths and methods of using catheters and sheaths. More particularly, the present invention relates to control handles for steerable catheters and sheaths and methods of manufacturing and using such handles.

BACKGROUND OF THE INVENTION

Catheters (i.e., catheters or sheaths) having conductive electrodes along a distal end are commonly used for intra-cardiac electrophysiology studies. The distal portion of such a catheter is typically placed into the heart to monitor and/or record the intra-cardiac electrical signals during electrophysiology studies or during intra-cardiac mapping. The orientation or configuration of the catheter distal end is controlled via an actuator located on a handle outside of the patient's body, and the electrodes conduct cardiac electrical signals to appropriate monitoring and recording devices that are operatively connected at the handle of the catheter.

Typically, these catheters include a generally cylindrical electrically non-conductive main body. The main body includes a flexible tube constructed from polyurethane, nylon or other electrically non-conductive flexible material. The main body further includes braided steel wires or other non-metallic fibers in its wall as reinforcing elements. Each electrode has a relatively fine electrically conductive wire attached thereto and extending through the main body of the catheter. The conductive wire extends from the distal end to a proximal end where electrical connectors such as plugs or jacks are provided to be plugged into a corresponding socket provided in a recording or monitoring device.

The distal portion of the main body is selectively deformed into a variety of curved configurations using the actuator. The actuator is commonly internally linked to the distal portion of the catheter by at least one actuation wire. Some catheters employ a single actuation wire, which is pulled (i.e., placed in tension) by the actuator in order to cause the distal portion of the main body to deform. Other catheters have at least two actuation wires, where the actuation of one wire (i.e., placing one wire in tension) results in the other wire going slack (i.e., the wire does not carry a compressive load). In such catheters, where the actuation wires are not adapted to carry compressive loads (i.e., the actuation wires are only meant to be placed in tension), the actuation wires are commonly called pull or tension wires.

To deform the distal end of the catheter into a variety of configurations, a more recent catheter design employs a pair of actuation wires that are adapted such that one of the actuation wires carries a compressive force when the other actuation wire carries a tensile force. In such catheters, where the actuation wires are adapted to carry both compressive and tension loads, the actuation wires are commonly called push/pull or tension/compression wires and the corresponding catheter actuators are called push-pull actuators. U.S. Pat. No. 5,861,024 to Rashidi, which issued Jan. 19, 1999, is representative of a push-pull actuator of this type, and the details thereof are incorporated herein by reference.

While many of the existing catheter actuators provide precise operation and good flexibility in movement of the distal portion of the body, the existing actuators often offer a range of distal portion displacement that is less than desirable. In other words, the amount of push/pull of the actuation wires (i.e., the steering travel) is often inadequate for the medical procedure being performed. The inadequacy of the steering travel typically results from the generally limited size of the actuator body, which is usually sized for receipt and manipulation between the thumb and index finger of a user's hand. Accordingly, a need exists to provide an improved actuating assembly for a catheter that increases the amount of steering travel associated with the actuator.

BRIEF SUMMARY OF THE INVENTION

The present invention, in one embodiment, is an electrophysiology, RF ablation, or similar catheter that includes an actuator that significantly increases the length of travel (i.e., steering travel) of the actuation wires. Throughout this specification, the term catheter is meant to include, without limitation, catheters, sheaths and similar medical devices.

The catheter includes a hollow flexible tubular body, a pair of actuation wires disposed in a side-by-side relationship in the body, a handle attached to a proximal end of the body, an actuator pivotally mounted to the handle, an arcuate internal gear rack disposed on the actuator, one or more pulleys pivotally mounted on the handle and coaxially coupled to a pinion gear engaged with the gear rack, and a guide block mounted within the handle.

The one or more pulleys include a first channel in which the first actuation wire resides and a second channel in which the second actuation wire resides. The actuation wires pass through holes in the guide block, which aligns the wires into their respective channels. The actuation wires enter into their respective channels on opposite sides of the axis of the one or more pulleys. As the actuator is pivoted relative to the handle, the gear rack engages the pinion gear and causes the pinion gear and the one or more pulleys to pivot. This causes one of the actuation wires to be in-hauled (i.e., wound about the one or more pulleys) and the other actuation wire to be paid-out (i.e., unwound from the one or more pulleys).

In one embodiment, the actuation wires are pull or tension wires. In another embodiment, the actuation wires are pull/push or tension/compression wires.

The present invention, in one embodiment, is an actuating assembly for an electrophysiology, RF ablation, or similar catheter. The actuating assembly includes a handle portion, a delta-shaped actuator, an arcuate gear rack, a pinion gear, and one or more pulleys.

The actuator is pivotally mounted near its apex to the handle and the arcuate gear rack extends laterally across a base portion of the actuator. The pinion gear is coaxially fixed to an axel and thereby pivotally mounted on the handle. The teeth of the pinion gear engage the teeth of the arcuate gear rack.

The one or more pulleys are coaxially fixed to the axel of the pinion gear and include a pair of peripheral channels. Each channel is adapted to receive one of a pair of actuation wires that extends from the tubular body of the catheter. The actuation wires enter their respective channels on opposite sides of the pivotal axis of the one or more pulleys.

As the actuator is pivoted relative to the handle, the gear rack rotates the pinion gear and, as a result, the one or more pulleys. As the one or more pulleys rotate, one of the actuation wires is wound about the one or more pulleys and the other actuation wire is unwound from the one or more pulleys.

The present invention, in one embodiment, is an actuating assembly for a catheter having first and second actuation wires. The assembly comprises an actuator pivotally attached to a handle and including a first rack, a second rack generally opposed to a third rack, and an axel. The axel includes an upper engagement portion and a lower engagement portion. The upper engagement portion is engaged with the first rack, and the lower engagement portion is located between, and engaged with, the second and third racks. Pivotal displacement of the actuator relative to the handle results in linear displacement of the second and third racks.

In one embodiment, the first actuation wire couples to an end of the second rack, and the second actuation wire couples to an end of the third rack. The linear displacement of the second rack is opposite in direction to the linear displacement of the third rack.

In one embodiment, the upper engagement portion is a pinion gear, the first rack is a gear rack, and the pinion gear and the gear rack each include teeth that cooperate with one another. In one embodiment, the gear rack is an arcuate internal gear. In another embodiment, the gear rack is an arcuate external gear.

In one embodiment, the lower engagement portion is a pinion gear, the second and third racks are gear racks, the pinion gear and the gear racks each include teeth, and the teeth of the pinion gear cooperate with teeth of the gear racks.

The present invention, in one embodiment, is an actuating assembly for a catheter including first and second actuation wires. The assembly comprises a first rack and an axel, which is pivotally coupled to a handle. The axel includes a first engagement portion. The first rack is in engagement with the first engagement portion and adapted to displace generally laterally relative to the handle. The generally lateral displacement of the first rack causes pivotal displacement of the axel and linear displacement the first and second actuation wires.

In one embodiment, the axel further includes a pulley assembly including a first channel adapted to receive the first actuation wire and a second channel adapted to receive the second actuation wire. Pivotal displacement of the axel causes the first actuation wire to be wound about the first channel while the second actuation wire is unwound from the second channel.

In another embodiment, the axel further includes a second engagement portion located between, and in engagement with, a second rack and a third rack that are opposed to each other. Pivotal displacement of the axel causes the second rack to displace proximally and the third rack to displace distally. The first actuation wire is coupled to an end of the second rack and the second actuation wire is coupled to an end of the third rack.

The present invention, in one embodiment, is a method of displacing a distal end of a tubular body of a catheter with an actuation handle coupled to a proximal end of the body. The body includes first and second actuation wires that extend through the body and into the handle. The method comprises displacing generally laterally relative to the handle a first rack against a first engagement portion pivotally coupled to the handle. This causes a pivotal motion in the engagement portion. This pivotal motion is converted into linear displacement of the first and second actuation wires.

In one embodiment, the conversion of the pivotal motion occurs via a pulley assembly that is coaxially coupled to the first engagement portion. The pulley assembly includes a first channel receiving a proximal end of the first actuation wire and a second channel receiving the proximal end of the second actuation wire.

In another embodiment, the conversion of the pivotal motion occurs via a second engagement portion that is coaxially coupled to the first engagement portion and positioned between, and in engagement with, a second rack and a third rack. The second rack is generally opposed to the third rack. The first actuation wire is coupled to an end of the second rack, and the second actuation wire is coupled to an end of the third rack.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 3b is a latitudinal cross section of the body taken along section line AA in FIG. 3a.

FIG. 3c is a latitudinal cross section of the body taken along section line BB in FIG. 3a.

FIG. 5 is a plan view of the handle depicted in FIG. 4.

FIG. 6 is a side elevation of the handle depicted in FIG. 4.

DETAILED DESCRIPTION OF THE INVENTION

Figure 1:
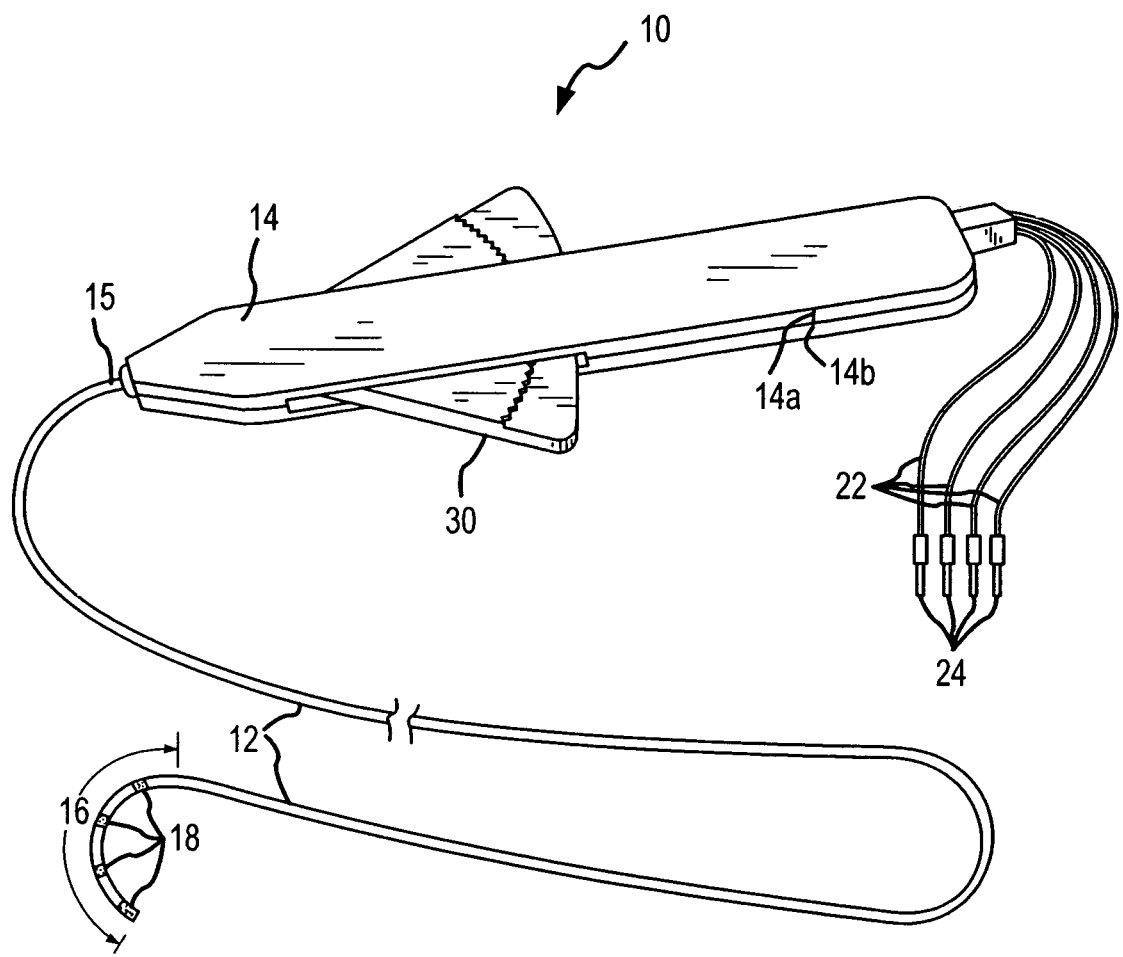
FIG. 1 is a perspective view of a catheter.

FIG. 1 is a perspective view of the present invention, which is, in one embodiment, an electrophysiology, RF ablation, or similar catheter 10 that includes an elongated flexible generally cylindrical hollow body 12 and an actuation handle 14 coupled to a proximal end 15 of the body 12. As will be understood from the following discussion, the catheter 10 is advantageous in that the actuation handle 14 is configured to significantly increase the steering travel of the distal end 16 of the body 12, as compared to prior art actuation handles. Throughout this specification, the term catheter is meant to include, without limitation, catheters, sheaths and similar medical devices.

In one embodiment, the body 12 is typically polyurethane, nylon or any suitable electrically non-conductive material. The body 12 serves as at least a portion of the blood-contacting segment of the catheter 10.

As illustrated in FIG. 1, the distal end 16 of the body 12 includes plural spaced electrodes 18. Each electrode 18 is connected to a fine electrical conductor wire 22 that extends through the body 12 and the handle 14 to connect to an electrical plug 24. Each electrical plug 24 extends from the proximal end of the handle 14 and is adapted to be inserted into a recording, monitoring, or RF ablation device.

As can be understood from FIG. 1, the distal end 16 of the body 12 is manipulated by selectively moving an actuator 30 that is movably mounted to the handle 14. In one embodiment, the actuator 30 is generally planar or flat, having a generally delta-shape with a wider portion near the rear of the handle 14. In one embodiment, the actuator 30 is wide enough to comfortably fit between the thumb and first finger of the catheter operator.

As indicated in FIG. 1, in one embodiment, the actuator 30 is received or sandwiched between an upper portion 14a and a lower portion 14b of the handle 14. It will be appreciated, however, that other actuator configurations may be used as alternatives to the delta-shaped actuator 30 without departing from the scope and intent of the present invention.

Figure 2:
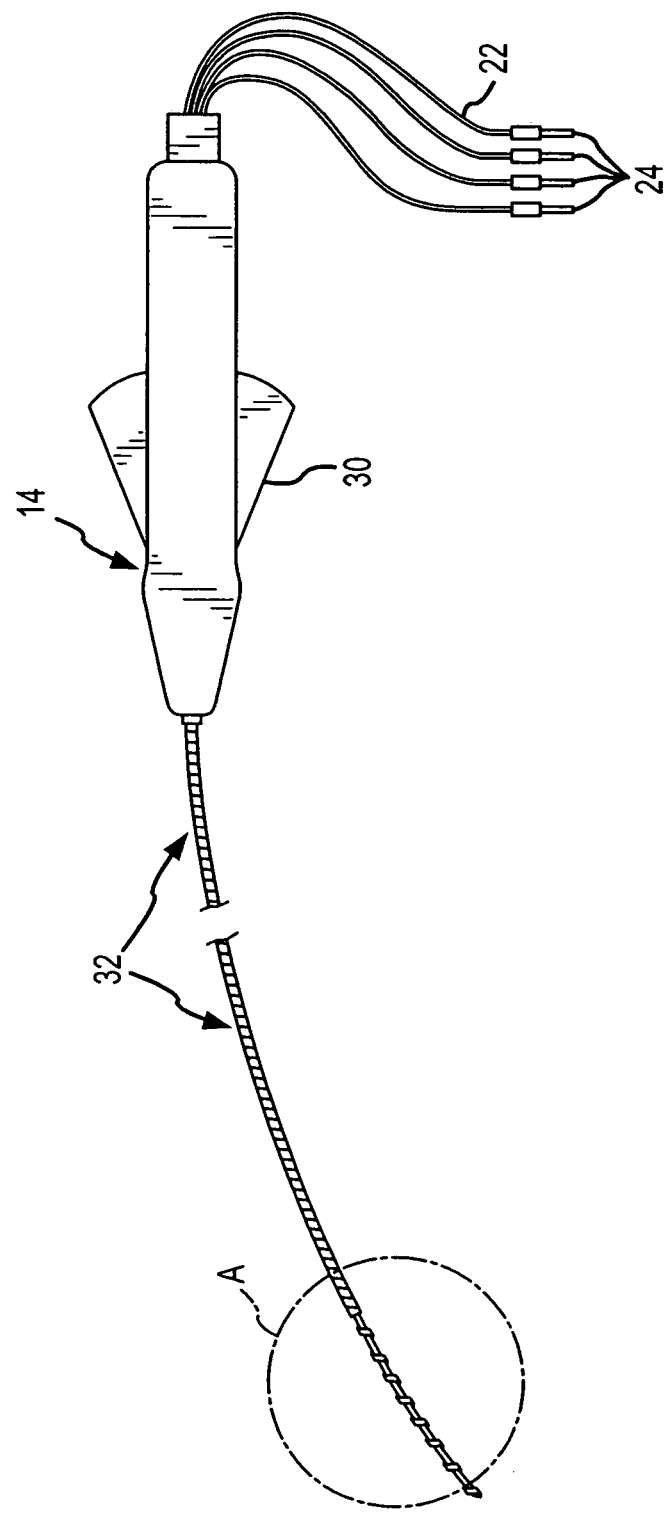
FIG. 2 is a perspective view of the catheter with the outer surface of the body removed to reveal the reinforcement of the body.
Figure 3A:
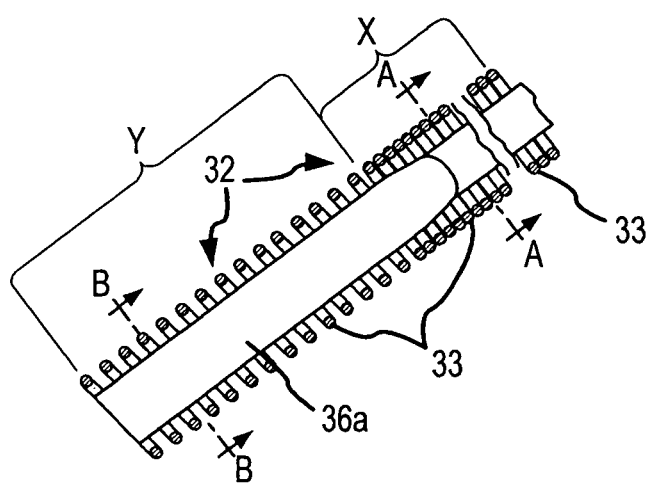
FIG. 3a is an enlarged longitudinal cross section of the distal portion of the body encircled by circle A in FIG. 2.
Figure 3B:
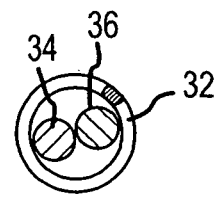
Figure 3C:
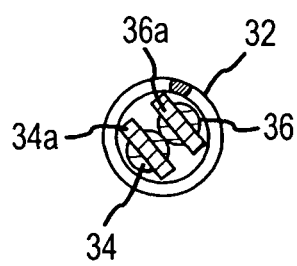

For a detailed discussion of the configuration of the body 12, reference is now made to FIGS. 2, 3a, 3b and 3c. FIG. 2 is a perspective view of the catheter 10 with the outer surface of the body 12 removed to reveal the reinforcement of the body 12. FIG. 3a is an enlarged longitudinal cross section of the distal portion 16 of the body 12 encircled by circle A in FIG. 2. FIG. 3b is a latitudinal cross section of the body 12 taken along section line AA in FIG. 3a. FIG. 3c is a latitudinal cross section of the body 12 taken along section line BB in FIG. 3a.

As can be understood from FIG. 2, in one embodiment, the outer surface of the body 12 surrounds an inner guide tube 32, which serves as a reinforcement for the body 12. As can be understood from FIG. 2 and as specifically indicated in FIG. 3a by region X, the inner guide tube 32 is formed as a tightly wound spring from the inner guide tube's point of connection with the handle 14 to a point near the distal end 16 of the tube 32. As specifically indicated in FIG. 3a by region Y, the windings 33 of a distal portion 16 of the inner guide tube 32 are wound in an open condition to provide a more easily bendable structure.

As indicated in FIGS. 3a-3c, a pair of flexible actuation wires 34, 36 are disposed in a side-by-side relationship inside the inner guide tube 32. In one embodiment, the actuation wires 34, 36 are formed from a super elastic nitinol flatwire. In one embodiment, the actuation wires 34, 36 are adapted to serve as pull or tension wires. In another embodiment, the actuation wires 34, 36 are adapted to serve as pull/push or tension/compression wires.

As indicated in FIGS. 3a and 3b, in one embodiment, the actuation wires 34, 36 have a generally circular cross-section that extends along the length of the inner guide tube 32 from a point near the tube's distal end towards, and into, the handle 14. As illustrated in FIGS. 3a and 3c, in one embodiment, the distal end 34a, 36a of each actuation wire 34, 36 also has a generally flattened ribbon-like cross section.

Figure 4:
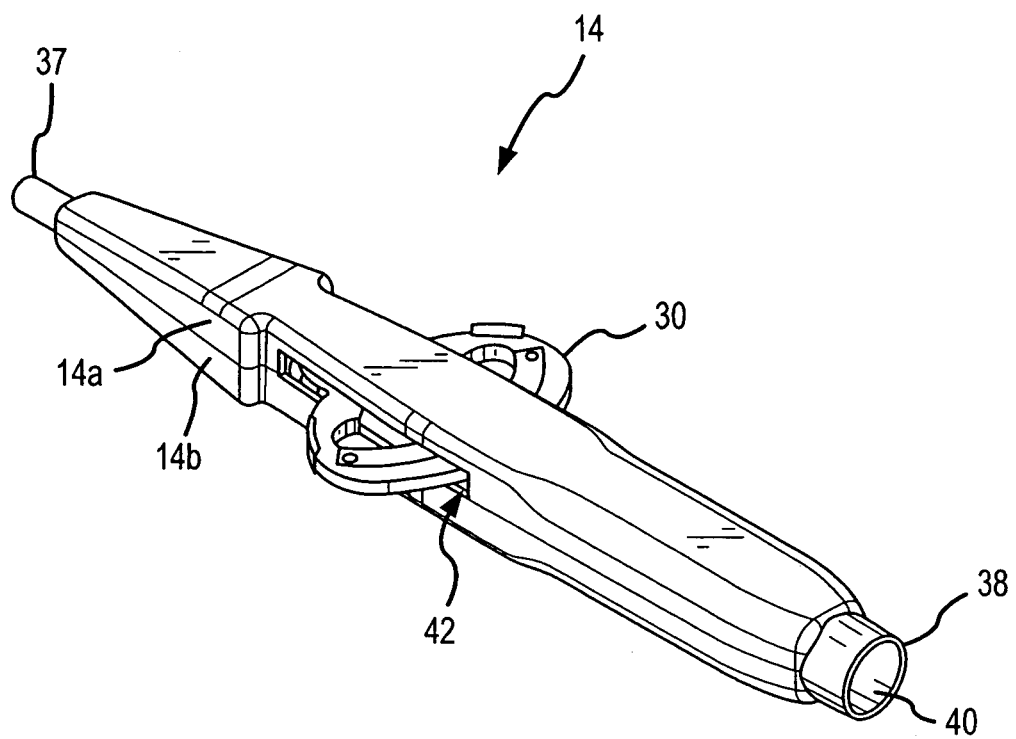
FIG. 4 is a rear perspective view of one embodiment of the handle.

For a detailed discussion of the catheter actuation handle 14 of the present invention, reference is now made to FIGS. 4-6. FIG. 4 is a rear perspective view of one embodiment of the handle 14. FIG. 5 is a plan view of the handle 14 depicted in FIG. 4. FIG. 6 is a side elevation of the handle 14 depicted in FIG. 4.

As indicated in FIG. 4, the handle 14 is generally cylindrical and includes a distal end 37 and a proximal end 38. The distal end 37 is adapted to couple to a proximal end 15 of the body 12 (see FIG. 1). The proximal end 38 has an opening 40 through which the wires 22 may exit on their way from the electrodes 18 to the electrical plugs 24 (see FIG. 1).

As shown in FIGS. 4 and 6, in one embodiment, the handle 14 has a slot 42 therein that is defined between the upper and lower portions 14a, 14b. The slot 42 allows the actuator 30 to pivotally displace side-to-side through the handle 14.

As illustrated in FIGS. 5 and 6, a cavity 44 (indicated by hidden lines) extends from the opening 40 in the proximal end 38 to an opening in the distal end 37. The cavity 44 provides a pathway through which the wires 22 may pass through the handle 14. In one embodiment, where the body 12 includes a lumen extending along its length, the cavity 44 serves as a pathway through which a catheter or other elongated medical device may be passed through the handle 14 and into a lumen of the body 12. As shown in FIG. 5, the actuation wires 34, 36 extend into the cavity 44 of the handle 14 from the body 12 and couple to elements of the actuation mechanism 46 of the handle 14.

Figure 7:
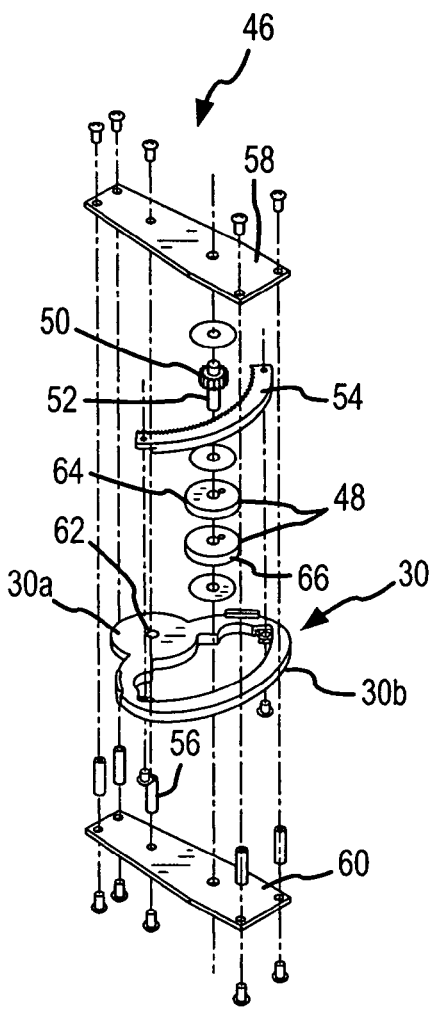
FIG. 7 is an exploded perspective view of the actuation mechanism of the handle.
Figure 8:
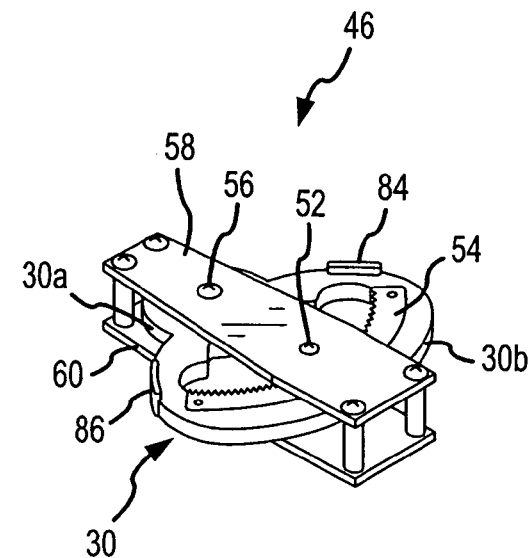
FIG. 8 is a perspective view of the assembled actuation mechanism of the handle.
Figure 9:
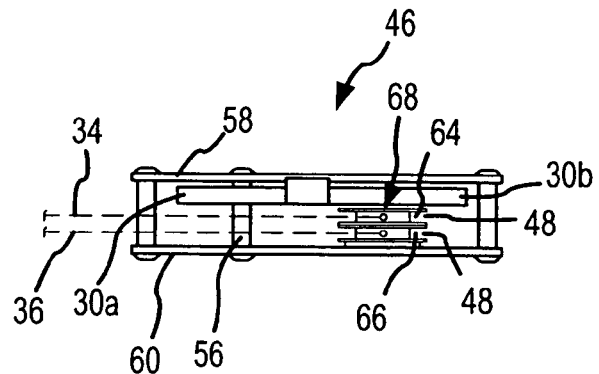
FIG. 9 is a side elevation of the assembled actuation mechanism of the handle.

For a detailed discussion of one embodiment of the actuation mechanism 46 of the handle 14, reference is now made to FIGS. 7-9. FIG. 7 is an exploded perspective view of the actuation mechanism 46 of the handle 14. FIG. 8 is a perspective view of the assembled actuation mechanism 46 of the handle 14. FIG. 9 is a side elevation of the assembled actuation mechanism 46 of the handle 14.

As shown in FIG. 7, in one embodiment, the actuation mechanism 46 includes one or more pulleys (i.e., a pulley assembly) 48, a pinion gear 50 mounted on an axel 52, an internal arcuate gear rack 54 attached to the actuator 30, a pivot 56, and upper and lower frame plates 58, 60. As shown in FIGS. 5, 8 and 9, the one or more pulleys 48 are fixedly mounted on the axel 52 of the pinion gear 50 in an arrangement that is coaxial with the axel 52 and pinion gear 50. The axel 52 extends between, and is pivotally coupled to, the upper and lower frame plates 58, 60. Accordingly, the axel 52, pinion gear 50 and one or more pulleys 48 may pivot about the axis of the axel 52 as an integral unit relative to the upper and lower frame plates 58, 60.

As illustrated in FIGS. 5, 8 and 9, the actuator 30, which is delta-shaped in one embodiment, is pivotally attached via a pivot hole 62 near its apex 30a to the pivot 56, which extends between the upper and lower frame plates 58, 60. The gear rack 54 is mounted on the actuator 30 such that the gear rack 54 extends laterally across the actuator 30 near the base end 30b of the actuator 30.

As shown in FIGS. 7 and 9, the one or more pulleys 48 provide a pair of parallel channels 64, 66 that extend about the circumferential periphery of the one or more pulleys (i.e., pulley assembly) 48. In one embodiment that is equipped with a single pulley 48, the single pulley 48 will have a pair of parallel channels 64, 66. In one embodiment that is equipped with a pair of pulleys 48, each pulley 48 will have a single channel 64 that is parallel to the single channel 66 of the other pulley 48.

As indicated in FIGS. 5 and 9, each actuation wire 34, 36 is received within its respective channel 64, 66. Each actuation wire 34, 36 is affixed within its respective channel 64, 66 via an attachment feature such as a hole 68 that the proximal end of the wire 34, 36 passes through and into the corresponding pulley 48.

As illustrated in FIG. 9, the channels 64, 66 are parallel to each other and, as a result, the actuation wires 34, 36 are vertically offset from each other as they extend from their respective channels 64, 66 towards the body 12. In one embodiment, as shown in FIG. 5, a guide block 70 (indicated by hidden lines) is provided within the cavity 44 of the handle 14 to align the actuation wires 34, 36 into the side-by-side coplanar relationship the actuation wires 34, 36 have when traveling through the body 12. The actuation wires 34, 36 exit their respective channels 64, 66, are properly aligned as they pass through holes in the guide block 70, and then enter the proximal end 15 of the body 12 on their way to the distal end 16 of the body. The guide block 70 also serves to properly align each actuation wire 34, 36 with its respective channel 64, 66 to prevent binding in the actuation mechanism 46.

In one embodiment, the guide block 70 is affixed to one or more of the frame plates 58, 60. In one embodiment, the guide block 70 is affixed to one or more of the handle portions 14a, 14b.

Figure 10:
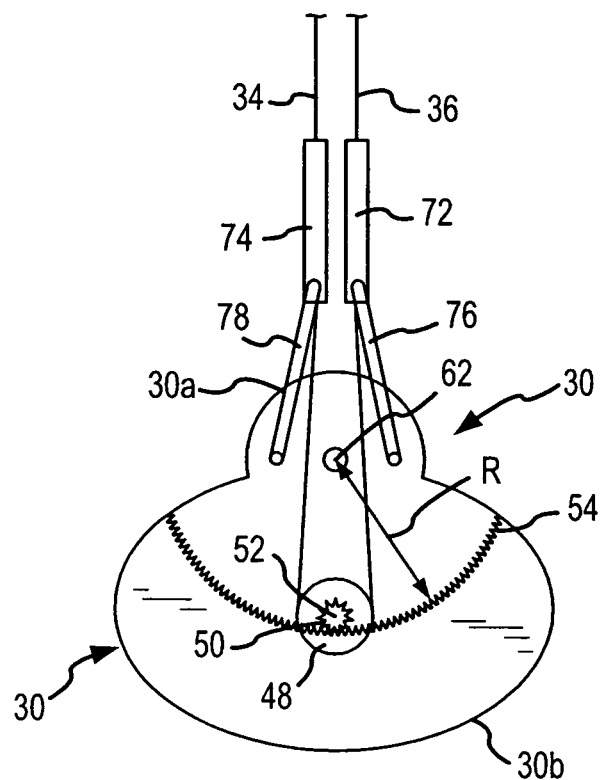
FIG. 10 is a plan view of an alternative actuator/guide configuration.

In one embodiment, as indicated in FIG. 10, which is a plan view of an alternative actuator/guide configuration, the guide block 70 illustrated in FIG. 5 is replaced with two movable guides 72, 74. As shown in FIG. 10, the proximal ends of the movable guides 72, 74 are coupled on opposite sides of the pivot 56 via links 76, 78. The movable guides 72, 74 are slidably received within the cavity 44 of the handle 14. Thus, as the actuator 30 is pivoted about the pivot 56 in a first direction, the first movable guide 72 is urged distally by its respective link 76, and the second movable guide 74 is urged proximally by its respective link 78. Conversely, pivoting the actuator 30 in a second direction opposite the first direction will cause the movable guides 72, 74 to reverse directions. Consequently, the movable guides 74, 76 are able to generally mimic the distal and proximal displacements of their respective actuation wires 34, 36, as described below.

As shown in FIG. 5, the pinion gear 50 engages the gear rack 54. Thus, when a user applies force to the actuator 30 to cause the actuator 30 to pivot about the pivot 56 in a first direction, the teeth of the gear rack 54 engage the teeth of the pinion gear 50 and cause the pinion gear 50 and the one or more pulleys 48 to pivot about the axis of the axel 52. The actuation wires 34, 36 enter into their respective channels 64, 66 on opposite sides of the pulley 48. Consequently, as the pulley 48 pivots, one actuation wire 34, 36 is hauled-in (i.e., wound about the pulley 48) and the other actuation wire 34, 36 is paid-out (i.e., unwound from about the pulley 48). Conversely, if the actuator 30 is driven in a second direction opposite the first direction, the movement of the pulley 48 and the actuation wires 34, 36 will reverse.

In one embodiment, where the actuation wires 34, 36 are pull or tension wires, the actuation wire 34, 36 being hauled-in will be placed into tension and the actuation wire 34, 36 being paid-out will deflect within the handle 14 (i.e., the wire 34, 36 will be placed in a no-load situation and will not carry a compressive load). In one embodiment, where the actuation wires 34, 36 are pull/push or tension/compression wires, the actuation wire 34, 36 being hauled-in will be placed into tension and the actuation wire 34, 36 being paid-out will push outward (i.e., the wire 34, 36 will carry a compressive load).

In one embodiment, the ends of the actuation wires 34, 36 that are attached to the channels 64, 66 are preferably pre-formed to the diameter of the pulley wheel 48. This is advantageous because it allows the pre-formed actuation wire 34, 36 to act as a tension spring and reduces the amount of force required to steer the catheter 10.

Figure 11:
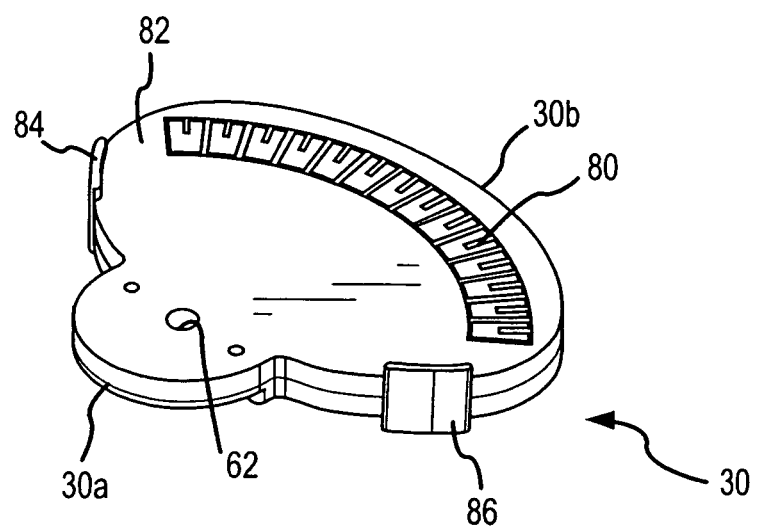
FIG. 11 is a top perspective view of the actuator.

In one embodiment, as shown in FIG. 11, which is a top perspective view of the actuator 30, a position indicator 80 extends generally arcuately across the top surface 82 of the actuator 30 near the actuator base end 30b. The position indicator 80 helps a user to track or measure the extent to which the actuator 30 has been displaced from a starting position. In one embodiment, the position indicator 80 is a three dimensional relief in the top surface 82 of the actuator 30 that may be engaged by an element extending from the top portion 14a of the handle 14. Such an engagement helps to positively maintain the actuator 30 in a displaced position without a conscious effort by the user.

As shown in FIG. 11, in one embodiment, finger-locating pads 84, 86 are provided at the lateral side surfaces of the actuator 30 for facilitating engagement with a user's fingers and aid in manipulation of the actuator 30. In one embodiment, the pads 84, 86 also serve as stops that abut against the sides of the handle 14 to prevent the actuator 30 from being overly extended through the handle 14.

As illustrated in FIG. 5, in one embodiment, the pulley 48 is generally centrally located laterally in the handle 14 so that generally equal travel of the actuator 30 (and thus rotation of the pulley 48) in opposite directions is provided. This, of course, may be altered if there is a particular need for increased travel or actuation in one direction versus another.

In one embodiment, the pinion 50 includes teeth or cogs that engage teeth or cogs on the rack 54. In another embodiment, the pinion 50 does not include teeth. Instead, the pinion 50 rides along a smooth surface provided on the rack 54 and frictional forces developed between the periphery of the pinion 50 and the rack 54 provide the rotational force for the pulley 48. Alternatively, the pulley 48 directly engages the rack 54, with or without teeth. Movement of the actuator 30 relative to the handle 14 results in movement (i.e., rotation) of the pulley 48 as the pinion 50 engages the rack 54. Rotation of the pulley 48 results in linear movement of the actuation wires 34, 36 through a substantially increased length of travel, as compared to the length of travel provided by prior art actuators.

As illustrated in FIG. 9, in one embodiment, the actuation wires 34, 36 are depicted as two separate wires residing in two separate channels 64, 66. However, in another embodiment, the actuation wires 34, 36 may be connected to one another to form one actuation wire carried in one or more channels.

Figure 12:
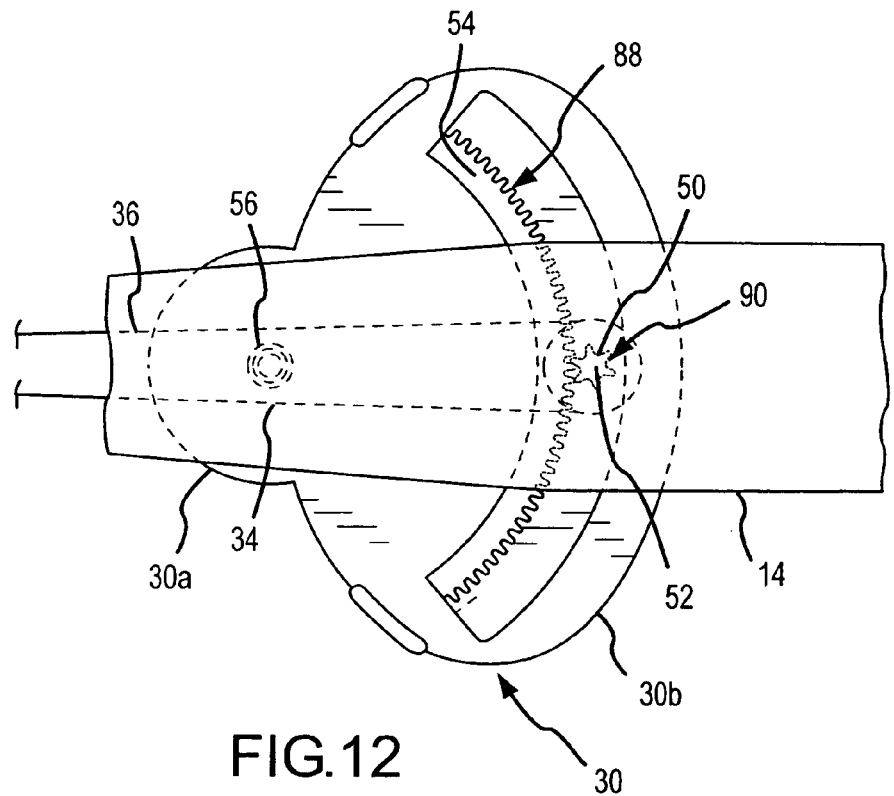
FIG. 12 is a plan view of the actuation mechanism employing an arcuate external gear and mounted in a handle.

As shown in FIG. 5, in one embodiment, the gear rack 54 is an arcuate internal gear (i.e., the teeth 88 of the gear rack 54 are on the inner circumferential edge of the gear rack 54), and the pinion gear 50 is positioned between the gear rack 54 and the pivot 56 such the teeth 90 of the pinion gear 50 engage the teeth 88 of the gear rack 54. However, in other embodiments, the gear rack 54 and pinion gear 50 will have other configurations. For example, as illustrated in FIG. 12, which a plan view of the actuation mechanism 46 mounted in a handle 14, in one embodiment, the gear rack 54 is an arcuate external gear (i.e., the teeth 88 of the gear rack 54 are on the outer circumferential edge of the gear rack 54), and the gear rack 54 is positioned between the pinion gear 50 and the pivot 56 such the teeth 90 of the pinion gear 50 engage the teeth 88 of the gear rack 54. In other embodiments, the gear rack 54 is linear or straight (i.e., non-arcuate) and the pinion gear 50 may be located on either side of the gear rack 54.

In one embodiment, the gear rack 54 has a pitch diameter of 2.187 inches, the pinion gear 50 has a pitch diameter of 0.281 inch, and the diameter of the pulley's channel 64, 66 is 0.500 inch. In other embodiments, the pitch diameter for the gear rack 54 will be between approximately 1.00 inch and approximately 5.00 inches, the pitch diameter for the pinion gear 50 will be between approximately 0.125 inch and approximately 1.00 inch, and the diameter of the pulley's channel 64, 66 will be between approximately 0.125 inch and approximately 2.00 inches. As indicated in FIG. 11, in one embodiment, the gear rack 54 is positioned relative to the pivot 62 such that the radius R between the pivot 64 and the semi-circle defined by the pitch diameter of the gear rack 54 is half of the pitch diameter of the gear rack 54.

Figure 14:
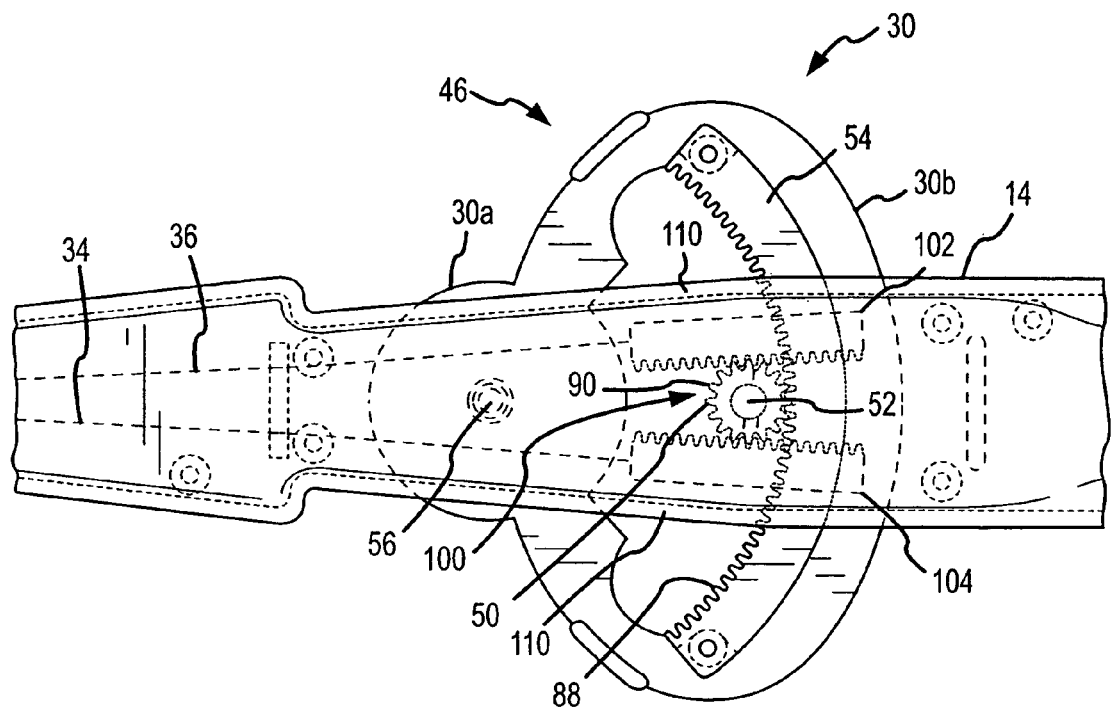
FIG. 14 is a plan view of the assembled actuation mechanism depicted in FIG. 13.
Figure 13:
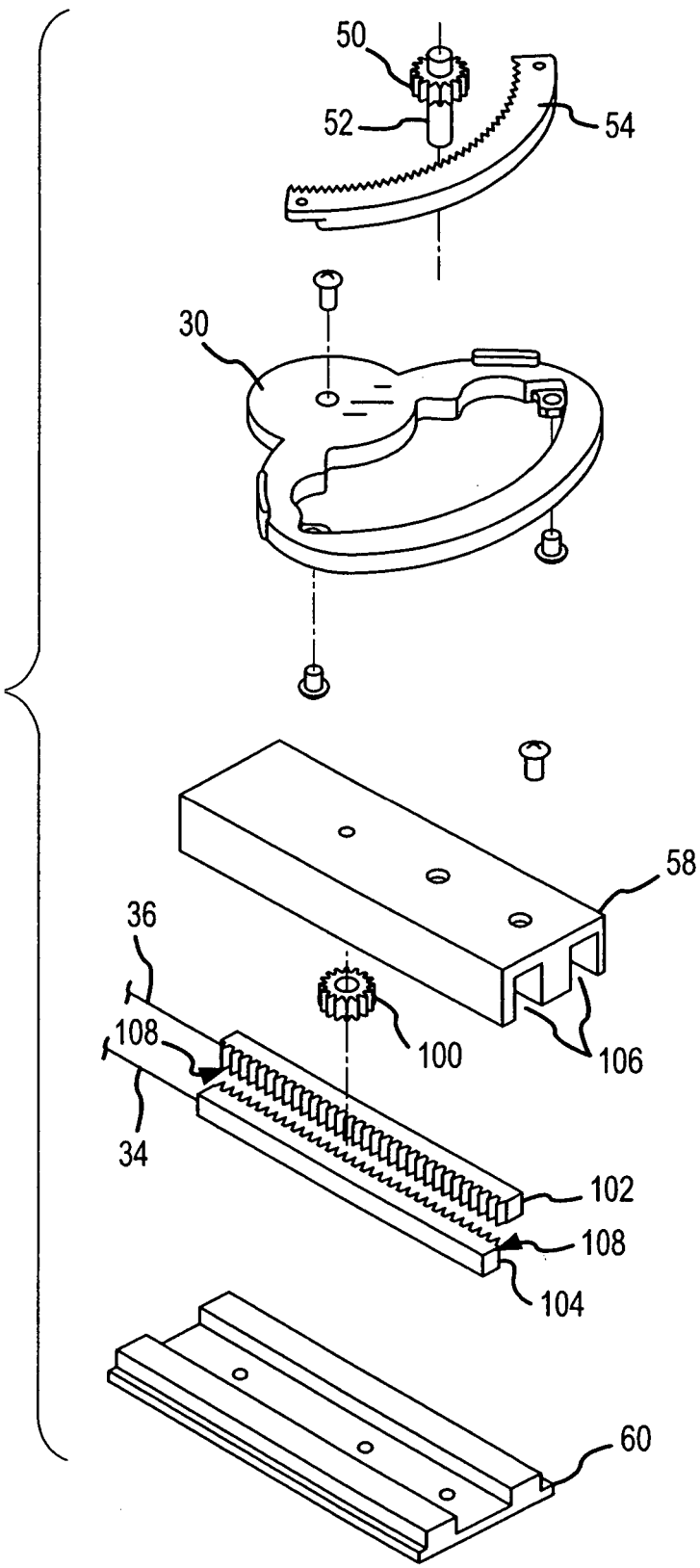
FIG. 13 is an exploded perspective view of an alternative embodiment of the actuation mechanism, wherein the mechanism drives opposed linear gear racks instead of pulleys.

For a discussion of another embodiment of the actuation mechanism 46 where the mechanism 46 drives opposed linear gear racks instead of pulleys, reference is now made to FIGS. 13 and 14. FIG. 13 is an exploded perspective view of the actuation mechanism 46. FIG. 14 is a plan view of the assembled actuation mechanism 46 mounted in a handle 14.

As shown in FIGS. 13 and 14, the actuation mechanism 46 includes an upper pinion gear 50 mounted on an axel 52, an internal arcuate gear rack 54 attached to the actuator 30, a pivot 56, a lower pinion gear 100, a pair of linear gear racks 102, 104, and upper and lower frame plates 58, 60. As can be understood from FIGS. 13 and 14, the lower pinion gear 100 is fixedly mounted on the axel 52 of the upper pinion gear 50 in an arrangement that is coaxial with the axel 52 and upper pinion gear 50. The axel 52 extends between, and is pivotally coupled to, the upper and lower frame plates 58, 60. Accordingly, the axel 52, upper pinion gear 50 and lower pinion gear 100 may pivot about the axis of the axel 52 as an integral unit relative to the upper and lower frame plates 58, 60.

As can be understood from FIGS. 13 and 14, the lower pinion gear 100 is positioned between the linear gear racks 102, 104, which are slidably located within rack slots 106 formed in the upper frame plate 58. The linear gear racks 102, 104 are oriented such that their teeth sides 108 oppose each other and engage with the teeth of the lower pinion gear 100. The lower frame plate 60 abuts against the bottom surfaces of the upper frame plate 58 to enclose the linear gear racks 102, 104 within their respective rack slots 106. The distal end of each linear gear rack 102, 104 is coupled to a proximal end of an actuation wire 34, 36.

As indicated in FIG. 13, in one embodiment, the linear gear racks 102, 104 are oriented generally parallel to each other. In another embodiment, as depicted in FIG. 14, the linear gear racks 102, 104 are oriented in a non-parallel configuration such that each linear gear rack 102, 104 is generally parallel to its immediately adjacent handle sidewall 110. In either embodiment, the linear gear racks 102, 104 are slidably displaceable within their respective rack slots 106.

As indicated in FIGS. 13 and 14, the actuator 30, which is delta-shaped in one embodiment, is pivotally attached via a pivot hole 62 near its apex 30a to the pivot 56, which extends into at least the upper frame plate 58. The gear rack 54 is mounted on the actuator 30 such that the gear rack 54 extends laterally across the actuator 30 near the base end 30b of the actuator 30.

As illustrated in FIG. 14, the upper pinion gear 50 engages with the arcuate internal gear rack 54 and the lower pinion gear 100 engages with the linear gear racks 102, 104. Thus, when a user applies force to the actuator 30 to cause the actuator 30 to pivot about the pivot 56 in a first direction, the teeth of the gear rack 54 engage the teeth of the upper pinion gear 50 and cause the upper pinion gear 50 and the lower pinion gear 100 to pivot about the axis of the axel 52. The teeth of the lower pinion gear 100 engage the teeth surfaces 108 of the linear gear racks 102, 104, proximally driving one of the linear gear racks 102 and distally driving the other linear gear rack 104. Conversely, if the actuator 30 is driven in a second direction opposite from the first direction, the lower pinion gear 100 will reverse the travel directions of each linear gear rack 102, 104.

As indicated in FIGS. 13 and 14, because each actuation wire 34, 36 is attached to the distal end of a linear gear rack 104, each wire 34, 36 will displace with its respective linear gear rack 104. For example, where the actuation wires 34, 36 are pull or tension wires, the actuation wire 34, 36 being pulled proximally by its proximally displacing linear gear rack 102, 104 will be placed into tension and the actuation wire 34, 36 being pushed distally by its distally displacing linear gear rack 102, 104 will deflect within the handle 14 (i.e., the wire 34, 36 will be placed in a no-load situation and will not carry a compressive load). In one embodiment, where the actuation wires 34, 36 are pull/push or tension/compression wires, the actuation wire 34, 36 being pulled proximally by its proximally displacing linear gear rack 102, 104 will be placed into tension and the actuation wire 34, 36 being pushed distally by its distally displacing linear gear rack 102, 104 will be pushed outward (i.e., the wire 34, 36 will carry a compressive load).

Although the present invention has been described with reference to preferred embodiments, persons skilled in the art will recognize that changes may be made in form and detail without departing from the spirit and scope of the invention.

What is claimed is:

1. A portable handheld device directly mechanically manipulated by an operator of a cardiac catheter including first and second actuation wires, comprising:
   an actuator moveably coupled to a handle and adapted to be directly mechanically manipulated by an operator;
   a pulley assembly pivotally attached to the handle and including a first channel for receiving the first actuation wire and a second channel for receiving the second actuation wire; and
   a rack secured to the actuator and engaged with an engagement portion of the pulley assembly,
   wherein when the actuator is manually displaced relative to the handle, the engagement between the rack and the pulley assembly causes the pulley assembly to pivot relative to the handle.

2. The device of claim 1, wherein the pulley assembly pivoting relative to the handle causes the first actuation wire to be wound about the first channel while the second actuation wire is unwound from the second channel.

3. The device of claim 1, wherein the engagement portion is a pinion gear, the rack is a gear rack, and the pinion gear and the gear rack each include teeth that cooperate with one another.

4. The device of claim 3, wherein the gear rack is an arcuate internal gear.

5. The device of claim 3, wherein the gear rack is an arcuate external gear.

6. The device of claim 1, wherein the first and second channels exist in parallel planes.

7. The device of claim 1, further comprising first and second guides coupled to the actuator and longitudinally displaceable within the handle, the first guide operatively receiving the first actuation wire and the second guide operatively receiving the second actuation wire.

8. The device of claim 1, wherein the actuator is pivotally coupled to the handle.

9. A portable handheld device directly mechanically manipulated by an operator of a cardiac catheter including first and second actuation wires, comprising:
   an axle pivotally coupled to a handle and including a first engagement portion; and
   a first rack in engagement with the first engagement portion and adapted to displace generally laterally relative to the handle,
   wherein the generally lateral displacement of the first rack causes pivotal displacement of the axle and linear displacement of the first and second actuation wires; and
   wherein the axle further includes a pulley assembly including a first channel adapted to receive the first actuation wire and a second channel adapted to receive the second actuation wire.

10. The device of claim 9, wherein the pivotal displacement of the axle causes the first actuation wire to be wound about the first channel while the second actuation wire is unwound from the second channel.

* * * * *